(12) United States Patent
Weikert et al.

(10) Patent No.: US 7,473,433 B2
(45) Date of Patent: Jan. 6, 2009

(54) PULMONARY DELIVERY OF POLYENE ANTIFUNGAL AGENTS

(75) Inventors: Michael Weikert, Belmont, CA (US); Marc S. Gordon, Sunnyvale, CA (US); Sandeep Kumar, Sunnyvale, CA (US); Bing Yang, Redwood City, CA (US); Razaq Sarwar, Fremont, CA (US)

(73) Assignee: Nektar Therapeutics, San Carlos, CA (US)

( * ) Notice: Subject to any disclaimer, the term of this patent is extended or adjusted under 35 U.S.C. 154(b) by 1294 days.

(21) Appl. No.: 10/032,239

(22) Filed: Dec. 21, 2001

(65) Prior Publication Data
US 2002/0177562 A1 Nov. 28, 2002

Related U.S. Application Data

(60) Provisional application No. 60/257,613, filed on Dec. 21, 2000.

(51) Int. Cl.
*A61K 9/14* (2006.01)
*A61K 9/50* (2006.01)

(52) U.S. Cl. ............... 424/489; 424/500; 424/501; 424/502

(58) Field of Classification Search ................ 424/489, 424/500, 501, 502
See application file for complete search history.

(56) References Cited

U.S. PATENT DOCUMENTS

| | | | |
|---|---|---|---|
| 4,016,254 A * | 4/1977 | Seager | ............... 424/497 |
| 4,027,015 A | 5/1977 | Weinstein et al. | |
| 4,223,130 A | 9/1980 | Weinstein et al. | |
| 4,359,462 A | 11/1982 | Weinstein et al. | |
| 4,822,777 A | 4/1989 | Abra et al. | |
| 4,877,619 A | 10/1989 | Richer et al. | |
| 4,895,719 A | 1/1990 | Ramachandran et al. | |
| 4,950,477 A | 8/1990 | Schmitt et al. | |
| 4,973,465 A | 11/1990 | Baurain et al. | |
| 5,032,582 A | 7/1991 | Abra et al. | |
| 5,049,388 A | 9/1991 | Knight et al. | |
| 5,049,389 A | 9/1991 | Radhakrishnan et al. | |
| 5,100,591 A | 3/1992 | Leclef et al. | |
| 5,194,266 A | 3/1993 | Abra et al. | |
| 5,389,373 A | 2/1995 | Davis et al. | |
| 5,534,502 A | 7/1996 | Seki et al. | |
| 5,776,904 A | 7/1998 | Seki et al. | |

(Continued)

FOREIGN PATENT DOCUMENTS

DE 19616573 11/1997

(Continued)

OTHER PUBLICATIONS

Diot et al., "Deposition of amphotericin B aerosols in pulmonary aspergilloma," Eur. Respir J., p. 1263-1268.

(Continued)

*Primary Examiner*—Shengjun Wang
(74) *Attorney, Agent, or Firm*—Guy Tucker (57) ABSTRACT

The present invention provides spray-dried polyene compositions for oral inhalation to the lung. The polyene antifungal compositions demonstrate superior aerosol properties, do not exhibit appreciable degradation of the polyene upon spray-drying, and are useful in the treatment and prophylaxis of both pulmonary and systemic fungal infections.

20 Claims, 1 Drawing Sheet

U.S. PATENT DOCUMENTS

| | | | |
|---|---|---|---|
| 5,965,156 A * | 10/1999 | Proffitt et al. | 424/450 |
| 5,976,574 A | 11/1999 | Gordon | |
| 5,985,248 A | 11/1999 | Gordon et al. | |
| 5,989,583 A | 11/1999 | Amselem et al. | |
| 6,001,336 A | 12/1999 | Gordon | |
| 6,077,543 A | 6/2000 | Gordon et al. | |
| 6,290,991 B1 | 9/2001 | Roser et al. | |

FOREIGN PATENT DOCUMENTS

| | | |
|---|---|---|
| EP | 634166 | 1/1995 |
| WO | WO 88/06450 | 9/1988 |
| WO | WO 88/07853 | 10/1988 |
| WO | WO 90/01873 | 3/1990 |
| WO | WO 90/06775 | 6/1990 |
| WO | WO 90/11754 | 10/1990 |
| WO | WO 93/03737 | 3/1993 |
| WO | WO 96/32149 | 10/1996 |
| WO | WO 97/03649 | 2/1997 |
| WO | WO 97/36577 | 10/1997 |
| WO | WO 97/48278 | 12/1997 |
| WO | WO 98/55148 | 12/1998 |
| WO | WO 99/00113 | 1/1999 |
| WO | WO 99/20261 | 4/1999 |
| WO | WO 99/44594 | 9/1999 |
| WO | WO 99/61003 | 12/1999 |
| WO | WO 00/06184 | 2/2000 |
| WO | WO 00/27359 | 5/2000 |
| WO | WO 00/61178 | 10/2000 |
| WO | WO 00/72827 | 12/2000 |
| WO | WO 01/02024 | 1/2001 |
| WO | WO 01/05379 | 1/2001 |
| WO | WO 01/13927 | 3/2001 |
| WO | WO 01/13956 | 3/2001 |
| WO | WO 01/32144 | 5/2001 |

OTHER PUBLICATIONS

Carroll E. Cross, "Amphotericin B aerosol for transiently immunocompromised hosts," Chest, vol. 106 (No. 3), p. 599-601.

Recihenspurner et al., "Significant reduction in the number of fungal infections after lung, heart-lung, and heart transplantation using aerosolized amphotericin b prophylaxis," transplantation, p. 627-628.

Gilbert et al., "Aerosolized Liposomal Amphotericin B for Treatment of pulmonary and systemic cryptococcus neoformans infection in mice," Antimicrobial agent, p. 1466-1471.

Stevens et al., "A randomized Trial of Intraconazole in Allergic Bronchopulmonary aspergillosis," New England J. of Med, p. 756-762.

Beyer et al., "Use of Amphotericin B Aerosols for the Prevention of Pulmonary Aspergillosis," Infection, p. 143-148.

Conneally et al., "nebulized amphotericin B as prophylaxis against invasive aspergillosis in granulocytopenic patients," Bone Marrow Transplantation, p. 403-406.

Allen et al., "Prophylactic efficacy of aeroslized liposomal (AMBisome) and non-liposomal (Fungizone) amphotericin B in murine pulmonary aspergillosis," J. Antimicorbial Chemo, p. 1001-1013.

Palmer et al., "Candidal Anastomotic infection in lung transplant recipients," J. Heart and Lung Transplant, p. 1029-1033.

Calvo et al., "Antifungal Prophylaxis during the early postoperative period of lung transplantation," Chest, p. 1301-1304.

Schwartz et al., "Aerosolized amphotericin B inhalations as prophylaxis of invacive aspergillus infections during prolonged," Blood, p. 3654-3661.

St. Georgiev., "Treatment and Development Therapeutics in Aspergillosis," Respiration, p. 291-302.

Dubois et al., "The physiologic Effectis of Inhaled Amphotericin B," Chest, p. 750-753.

* cited by examiner

FIGURE.

PULMONARY DELIVERY OF POLYENE ANTIFUNGAL AGENTS

This application claims the benefit of priority of U.S. Provisional Patent Application Ser. No. 60/257,613, the contents of which is incorporated herein by reference in its entirety.

FIELD OF THE INVENTION

The present invention relates to spray-dried polyene compositions, and to methods for making and administering such compositions. In particular, the invention is directed to polyene powder compositions which possess a number of notable features, making them advantageous for oral inhalation to the lung for the treatment and/or prophylaxis of pulmonary and systemic fungal infections. The polyene is surprisingly stable (i.e., exhibits minimal chemical degradation) upon spray-drying, and the resulting powder possesses superior aerosol properties (low MMAD, excellent dispersibility), even in the absence of stabilizing carriers or excipients.

BACKGROUND OF THE INVENTION

Pulmonary fungal infections, which are associated with significant levels of morbidity and mortality, represent a major medical challenge. In recent years, the frequency and seriousness of fungal infections has increased, due to increasing numbers of organ transplantations, aggressive antineoplastic therapy regimens, and patients suffering from immune diseases such as HIV. Fungal infections of the lung, e.g., fungal pneumonia, allergic bronchopulmonary aspergillosis and other infections caused by *Aspergillus*, are typically treated by direct intracavitary instillation, oral, intraperitoneal, or intrapleural administration, or intravenous infusion of one or more antifungal agents such as amphotericin B (St. Georgiev, V., Respiration, 59:291-302 (1992). Unfortunately, serious drawbacks exist with each of these commonly employed routes of administration as described more fully below.

Direct intracavitary instillation, an invasive procedure, is usually accomplished by repeated transthoracic injections into the cavity. Drawbacks of intracavitary administration can include poor tolerance (the development of fever), risk of pheumothorax, and relapse of infection in the cavity (Glimp, RA, et al., Arch Intern Med, 143:303-308 (1983). In general, endobronchial administration of antifungals has met with minimal success (Henderson, AH, et al., Thorax, 23:519-523 (1968)). Oral formulations tend to be absorbed very poorly from the gastrointestinal tract, and like intravenous therapy are limited by associated dose-dependent drug toxicity, which (i) limits the intravenous dose that can be administered, and (ii) can result in unpleasant or even life threatening complications such as nephrotoxicity and normochromic anemia. Some of the disadvantages of intravenous therapy using conventional antifungal formulations have been addressed by the development of liposomal compositions such as ambisome (a liposomal formulation of amphotericin B), which, when administered by injection, does not display serious toxicity such as renal tubular damage, and allows the administration of doses which exceed those used in conventional formulations (Hay, R J in Recent Progress in Antifungal Chemotherapy. New York, Marcel Dekker, 1992 (323-332)).

Oral or intravenously administered systemic antifungals for treating respiratory infections suffer from an added disadvantage—the uncertainty of drug penetration into the lung tissue and infected secretions. This is important since effective drug therapy for lower respiratory tract infections depends upon not only the susceptibility of the infecting microorganisms, but upon the attainment of effective antifungal concentrations in the lung tissue and mucus. In an attempt to address this problem, inhalation therapy using nebulizer-generated aerosols has been investigated, using antifungals such as amphotericin B (Beyer, J., et al., Infection, 22:2, 143 (1994); Calvo, V., et al., Chest, 115:5 (1999); Dubois J., et al., Chest, 108:3, 750-753 (1995); Diot, P. et al., Eur Respir J., 8:1263-1268 (1995)).

Aerosolized pharmaceutics for inhalation can be delivered in a variety of different forms, including nebulized sprays, pressurized powder formulations, and non-pressurized powder formulations. Several drawbacks exist for both liquid and pressurized formulations. Disadvantages of liquid formulations include the chemical instability of certain active agents in solution (polyenes in particular), the high potential for microorganism contamination, and the use of cumbersome liquid nebulizers. Pressurized powder formulations containing a compressed gas or liquefied gas propellant have the disadvantages of employing ozone depleting agents in the case of CFCs, or green house gases in the case of HFCs. Further, liquid gas propellant typically cannot accommodate the quantities of antifungal agent required to achieve high levels of fungistatic/fungicidal activity locally at the site of infection. Pressurized powder formulations can also exhibit a high level of variability in the dose that is delivered to the lungs, due the inability of patients to consistently coordinate the firing of the inhaler to generate the aerosol with the appropriate cycling of the inhalation. Achieving adequate solubilization or suspension of antifungal agents such as the polyene, amphotericin B, in the liquefied gas propellant can also be problematic.

Thus, in view of the problems noted above using conventional antifungal therapies, it would be desirable to provide an inhaleable, non-pressurized antifungal dry powder for localized delivery to the lung, for both the treatment of pulmonary fungal infections and for therapy of systemic fungous diseases. Inhaleable dry powder formulations can provide high concentrations of antifungal agent in the lung with negligible concentrations in the blood and body tissues. Moreover, by utilizing a topical administration route, most of the toxicities that are associated with systemic antifungal agents (including nephrotoxicity, convulsions, fever, and chills, among others) can be minimized or avoided. Inhalation of antifungals using a dry powder inhaler maximizes the convenience and speed of administration, and overcomes the disadvantages of alternative inhalation therapies as described above.

Unfortunately, the development of chemically stable dry powders of an antifungal agent such as amphotericin B that also possess the physical properties necessary for aerosolization (e.g., high dispersibilities which remain stable over time, appropriate aerodynamic size) remains a technical challenge.

SUMMARY OF THE INVENTION

The present invention is directed to inhaleable, spray dried powder formulations of polyene antibiotics. While polyenes such as amphotericin are highly effective antifungal compounds, they also possess very low solubilities in water and in conventional organic solvents such as chloroform. Thus, formulation of these compounds outside of dry mixing is extremely difficult. Although the solubility of the polyene, amphotericin, can be increased under extreme conditions of pH, such conditions typically lead to significant levels of degradation of drug and are usually considered undesirable for the formation of powders for direct administration to the lung. Thus, the inventors were faced with the challenge of trying to find conditions for spray drying the highly insoluble drug, amphotericin, that (i) did not promote high levels of degradation of drug, (ii) were economically practical, and (iii) resulted in the formation of aerosolizable particles suitable for inhalation. While finding a solution to one of these problems was rather straightforward, arriving at a spray drying method in which all of these factors were balanced to produce a chemically stable and highly dispersible powder was a technical challenge.

In an effort to address these problems, the present invention provides methods for spray drying polyene antifungal agents that result in the formation of chemically stable yet highly dispersible powders. That is to say, the antifungal powders of the invention have excellent aerosol characteristics, such that they are reproducibly prepared and can be efficiently administered by inhalation to the lung, while exhibiting good chemical and physical stability.

In one aspect, the present invention provides a method for preparing a spray dried polyene, such as amphotericin B or nystatin, for oral administration to the lung. The method includes the steps of dissolving a polyene antifungal agent in an acidified solvent and spray drying the polyene solution to form an inhaleable powder containing no more than about 10% polyene degradation products and characterized by an emitted dose of greater than 60%.

In one embodiment of this aspect of the invention, the acidified solvent comprises an acidified alcohol such as methanol or ethanol, aqueous methanol, or aqueous ethanol. In yet another embodiment, the pH of the acidified solvent ranges from about 3.5 to about 5. In a preferred embodiment of the invention, the polyene is dissolved in the acidified solvent to an extent greater than about 1 mg/mL or preferably to an extent greater than about 2-3 mgs/mL.

In yet another embodiment of the method, the acidic polyene-containing solution is maintained at a temperature below 25° C. prior to and/or during spray drying. In a preferred embodiment, the acidic polyene-containing solution is maintained at a temperature below 8° C. and even more preferably below 0° C. prior to and/or during spray drying.

In yet another embodiment of the method, the polyene-containing solution to be spray dried contains at least about 50% polyene by weight based upon the total dissolved solids content of the solution.

In yet another embodiment of the method, the polyene-containing solution is absent lipid or polymeric encapsulating agents.

In yet another aspect, provided is a method for preparing a spray dried polyene powder for oral inhalation to the lung in which a polyene antifungal compound is suspended in an aqueous solvent to form a suspension, which is then wet milled, and spray dried. The resulting inhaleable powder contains no more than about 10% polyene degradation products (and typically less than that) and is characterized by an emitted dose greater than about 60%.

In one particular embodiment of this aspect of the invention, the antifungal compound is homogenized to form a homogenized suspension prior to spray drying.

In yet another embodiment of this aspect of the invention, the spray dried powder is exposed to moisture prior to packaging (i.e., either during or post spray drying) to decrease or maintain the aerodynamic diameter of the particles preferably below about 5 microns.

In one particular embodiment, the powder is spray dried using a wet drying gas, such as wet air, argon or nitrogen. Alternatively, the spray dried powder is exposed, post spray drying, to an amount of moisture sufficient to form a powder having a moisture content ranging from about 3% to about 10% by weight.

In a preferred embodiment, the spray dried powder is exposed or maintained at a relative humidity greater than about 5% prior to packaging.

In yet another embodiment, the spray dried powder is aerosolized in a current of air.

Also provided are polyene dry powders produced by either of the above methods.

In yet another aspect, the invention provides a spray-dried powder composition suitable for oral inhalation to the lung comprising a therapeutically effective amount of a polyene antifungal compound, where the composition comprises no more than about 10% polyene degradation products and is characterized by an emitted dose greater than about 60%.

In one particular embodiment of the invention, the spray dried powder is composed of particles having an MMAD of less than about 5 microns, and preferably less than about 3.5 microns.

In yet another embodiment, the spray dried powder is non-proteinaceous.

In yet another embodiment of this aspect of the invention, the polyene is non-encapsulated.

In one particular embodiment, the spray dried polyene powder substantially comprises neat polyene antifungal compound (i.e., lacks additional additives and/or excipients). In an alternative embodiment, the spray dried powder composition further comprises a pharmaceutically acceptable excipient. Preferred excipients are buffers, leucine and trileucine.

In yet another embodiment, the spray dry powder is composed of at least about 30% by weight polyene.

In yet another aspect, provided herein in a method for preparing an inhaleable spray dried powder which includes the steps of spray drying a solution or suspension containing an active agent to form particles having a particular MMAD, is an improvement wherein the powder is exposed, either during or after spray drying, to moisture in an amount effective to reduce the MMAD of the particles over the MMAD of the particles formed in the absence of such an exposing step. This method is particularly applicable to powders comprising one or more molecular components having a large percentage of water binding sites.

The invention further encompasses aerosolized powder compositions as described above.

The invention further encompasses a method for treating or preventing fungal infection in a mammalian subject in need thereof by administering to the subject by oral inhalation a spray-dried polyene antifungal powder as described herein.

These and other objects and features of the invention will become more fully apparent when the following detailed description is read in conjunction with the accompanying figures and examples.

DETAILED DESCRIPTION OF THE INVENTION

I. Definitions

The following terms as used herein have the meanings indicated.

"Antifungal compound" refers to any compound or its pharmaceutically acceptable salt having fungistatic and/or fungicidal properties.

"Polyene" refers to an organic compound containing a series of double bonds that are typically, but not necessarily, conjugated.

"Pharmaceutically acceptable salt" includes, but is not limited to, salts prepared with inorganic acids, such as chloride, sulfate, phosphate, diphosphate, hydrobromide, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, lithium, sodium, potassium, barium, calcium, aluminum, and ammonium (including substituted ammonium). Pharmaceutically acceptable salts of antifungal compounds have the same general pharmacological properties as the parent compound from which they are derived.

A "pharmaceutically acceptable ester" of a carboxylic acid-containing antifungal compound is a hydrolyzable ester having the same general pharmacological properties as the acid from which it is derived. Such esters include unsubstituted and substituted alkyl, aryl and phosphoryl esters. Non-limiting examples of pharmaceutically-acceptable esters include, for example, isopropyl, tertiarybutyl, 2-chloroethyl, 2,2,2-trichloroethyl, 2,2,2-trifluoroethyl, p-toluenesulfonylethyl, glycyl, sarcosyl, benzyl, phenyl, 1,2-hexanoylglyceryl, para-nitrophenyl, 2,2 dimethyl-1,3-dioxolene-4-methyl, isopentenyl, o-carbomethoxyphenyl, piraloyloxymethylsalicylyl, diethylamidophosphoryl, pivaloyloxymethyl, acyloxymethyl, propionyloxymethyl, isobutyryloxymethyl, dodecyl, octadecyl, and isopropyloxymethyl.

"Relative pulmonary bioavailability" is the percentage of an antifungal dose (for the treatment of systemic fungal disease) that is deposited in the lungs that is absorbed and enters the blood of a mammal relative to the percent that is absorbed into the blood from an intravenous injection site. Representative model systems for determining relative pulmonary bioavailabilities include rat, rabbit, and monkey. The antifungal compositions of the invention are, in one respect, characterized by a relative pulmonary bioavailability of at least about 3% in plasma or blood, with relative pulmonary bioavailabilities generally ranging from about 5% to about 20% or greater. Relative pulmonary bioavailability may be estimated by measuring absorption from direct intratracheal administration or by inhalation of an antifungal composition.

"Amino acid" refers to any compound containing both an amino group and a carboxylic acid group, and is meant to encompass pharmaceutically acceptable salts thereof. Although the amino group most commonly occurs at the position adjacent to the carboxy function, the amino group may be positioned at any location within the molecule. The amino acid may also contain additional functional groups, such as amino, thio, carboxyl, carboxamide, imidazole, etc. The amino acid may be synthetic or naturally occurring, and may be used in either its racemic, or optically active (D-, or L-) forms, for example, as a single optically active enantiomer or as any combination or ratio of enantiomers.

"Enhancer" refers to a compound that enhances the absorption of an antifungal compound through mucosal membranes, e.g., of the lung.

"Dry powder" refers to a powdered composition that contains finely dispersed solid particles that are capable of (i) being readily dispersed in an inhalation device and (ii) inhaled by a subject so that a portion of the particles reach the lungs to permit penetration into the alveoli. Such a powder is considered to be "respirable" or suitable for pulmonary delivery. Unless otherwise stated, a "dry powder composition for delivery to the deep lung" is one that, when aerosolized, is administered as dry powder particles. A dry powder in accordance with the invention is preferably a non-liposomal powder. Additionally, a dry powder of the invention is one that is preferably absent polymeric encapsulating agents or polymeric matrices.

"Oligopeptides" are peptides comprising two to ten amino acid residues (dimers to decamers).

"Peptide" as used herein is meant to encompass both naturally occurring and artificially constructed polypeptides in which individual amino acid units are linked together through the standard peptide amide bond (the carboxyl group of one and the amino group of another) and having a molecular weight between about 1,000 and about 6000.

"Protein" refers to a particular class of polypeptides having molecular weights ranging from about 6000 to more than 1,000,000.

A "leucyl-containing excipient comprising from 1 to 5 amino acid residues" includes the amino acid leucine, and oligomers composed of from 2 to 5 amino acid residues, one or more of which is leucine.

A powder comprising essentially "neat antifungal polyene" is one substantially lacking any other excipients or additives besides the antifungal compound, i.e., contains less than about 3% by weight non-antifungal component(s), preferably less than about 2% by weight non-antifungal component, more preferably less than 1% by weight antifungal component, and in some cases comprises 100% antifungal compound.

"Emitted dose" provides an indication of the delivery of a dry powder from the mouthpiece of a suitable inhaler device after a firing or dispersion event. More specifically, the ED is a measure of the percentage of powder which is drawn out of a unit dose package and which exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-determined parameter, and is typically determined in-vitro using a device set up which mimics patient dosing. To determine a ED value, a nominal dose of dry powder, typically in unit dose form, is placed into a suitable dry powder inhaler (such as that described in U.S. Pat. No. 5,785,049, assigned to Inhale Therapeutic Systems, Inc.) which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing dosage form placed into an inhalation device, if dispersion of the powder results in the recovery of 4 mg of powder on a tared filter as described above, then the ED for the dry powder composition is: 4 mg (delivered dose)/5 mg (nominal dose)×100=80%. For homogenous powders, ED values provide an indication of the delivery of therapeutic moiety (i.e., antifungal compound) from an inhaler device after firing. Similarly for MDI and nebulizer dosage forms, the ED corresponds to the percentage of drug which is drawn from a dosage form and which exits the mouthpiece of an inhaler device.

"Fine particle fraction" or "FPF" provides a measure of aerosolized powder delivery efficiency from a unit dosage form (e.g., a blister pack) to the deep lung, and is determined experimentally using a short stack Anderson cascade impactor operated at a vacuum of 28.3 liters per minute. The FPF is defined as the total mass, in milligrams, of aerosolized powder having a particle size less than 3.3 micrometers, relative to the mass of powder contained in a unit dosage form, in milligrams, and expressed as a percentage.

$$FPF = \frac{\text{total aerosolized powder mass less than 3.3 } \mu m \text{ (mg)}}{\text{unit dosage form fill mass}}$$

A "dispersible" powder is one having an ED value of at least about 30%, preferably at least about 35%, more preferably at least about 40%, and most preferably at least about 50%. Powders of the present invention are highly dispersible, having ED values of at least 60% or greater. Dispersibility, as used herein, refers to the dispersibility of a dry powder in a gas stream (e.g., a stream of air) unless otherwise indicated.

A dry powder composition suitable for "inhalation therapy", is one which, when aerosolized, may be (i) readily dispersed in an inhalation delivery device, and (ii) inspired through either the mouth by a mammalian subject so that at least a portion of the particles are absorbed into the lung.

A composition suitable for "oral pulmonary administration" comprises particles at least a portion of which, when delivered via inhalation by the mouth, reach the tissues of the lung, including the deep lung.

"Mass median diameter" or "MMD" is a measure of mean particle size, since the powders of the invention are generally polydisperse (i.e., consist of a range of particle sizes). MMD values as reported herein are determined by laser diffraction, although any number of commonly employed techniques can be used for measuring mean particle size (e.g., centrifugal sedimentation, electron microscopy, light scattering).

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

"Pharmaceutically acceptable excipient or carrier" refers to an excipient that may be included in the particles of the invention and taken into the lungs in association with the particles with no significant adverse toxicological side effects (e.g., toxicity, irritation, and allergic response) to the subject, and particularly to the lungs of the subject.

"Pharmacologically effective amount" or "physiologically effective amount" of an antifungal powder is the amount of an antifungal compound present in a particulate dry powder composition as described herein that is needed to provide a therapeutic or prophylactic level of antifungal agent, either in the bloodstream or at the infected tissue site (depending upon the fungus to be treated) when such composition is administered by inhalation over a particular duration of time. The precise amount will depend upon numerous factors, e.g., the particular antifungal(s) contained in the powder, the potency of the antifungal compound employed, the condition being treated, the delivery device employed, the physical characteristics of the powder, intended patient use (e.g., the number of doses administered per day), and patient considerations, and can readily be determined by one skilled in the art, based upon the information provided herein. Recommended dosage ranges will be described in greater detail below.

"Bulk density" refers to the density of a powder prior to compaction (i.e., the density of an uncompressed powder), and is typically measured by a well-known USP method.

The "extent of degradation" of a polyene is the percentage of polyene contained in the dry powder composition determined to be chemically modified from the intact starting material, as determined by a suitable chemical assay (e.g., NMR, HPLC, etc.); 100% of the polyene remaining chemically intact during the spray drying process represents an extent of degradation of 0%.

Inhaleable Antifungal Compositions

The present invention provides compositions for the oral pulmonary delivery of polyene antifungal compounds. These compositions overcome many of the problems and inconveniences encountered heretofore in administering antifungals, and particularly polyene antifungals, by other routes (e.g., poor absorption from the gastrointestinal tract, severe toxic side effects, the requirement for hospitalization during intravenous therapy, etc.) particularly for treating and/or preventing systemic and/or pulmonary fungal diseases. The powder compositions described herein (i) are readily dispersed by dry powder delivery devices (i.e, demonstrate superior aerosol properties), (ii) exhibit good physical stability during powder manufacture, processing, and storage, and (iii) are reproducibly prepared with minimal degradation of polyene. Inhaleable polyene antifungal compositions in accordance with the invention are preferably dry powders (i.e., for use in dry powder inhalers (DPIs).

The dry powder compositions according to the present invention generally include one or more antifungal compounds, one being a polyene, and optionally a pharmaceutically acceptable excipient. Dry powders composed of neat polyene antifungal agent (i.e., respirable powders composed of one or more polyene antifungal compounds and essentially lacking any additional excipients or additives) and demonstrating good aerosol properties have been prepared (see, e.g., Examples 1, 2, 5, 6, and 8). The challenge facing the inventors was to balance the factors influencing chemical degradation of the polyene antifungal compound during liquid formulation preparation and spray-drying (polyenes are prone to chemical degradation, especially at elevated temperatures) with those affecting aerodynamic particle size and particle dispersibility. Surprisingly, the inventors have prepared powders in which all of these factors are optimized—extent of degradation of polyene, high dispersibilities, and small aerodynamic particle sizes. (See the Examples). Moreover, it is unusual to prepare powders characterized by both high emitted dose values and low aerodynamic particle sizes, since these factors often work in opposing directions. That is to say, particles having good dispersibilities are often characterized by large aerodynamic sizes, since larger primary particles, which exhibit less cohesive force, tend to agglomerate less and thus disperse better.

Moreover, the preparation of antifungal powders having superior aerosol properties, as characterized by high ED values and small aerodynamic sizes, in the absence of additives or dispersing agents for improving aerosol properties, is particularly surprising (Yamashita, C., et al., Respiratory Drug Delivery VI, p. 483-485 (1998)), particularly for polyene fungal powders where the antifungal powder is non-proteinaceous.

Specific components of antifungal dry powders suitable for delivery to the lung will now be described.

A. Antifungal Compounds

Antifungal compounds for use in the dry powders of the invention are those having fungistatic or fungicidal properties when administered by oral inhalation to the lung. Preferred antifungal compounds are those characterized by a polyene chemical structure, such as amphotericin B, nystatin, hamycin, natamycin, pimaricin, and ambruticin, and pharmaceutically acceptable derivatives and salts thereof. Preferred for use in the present invention are amphotericin B and nystatin.

Other suitable antifungal compounds for use in the powders of the invention include acrisocin, aminacrine, anthralin, benanomicin A, benzoic acid, butylparaben, calcium unidecyleneate, candicidin, ciclopirox olamine, cilofungin, clioquinol, clotrimazole, ecaonazole, flucanazole, flucytosine, gentian violet, griseofulvin, haloprogin, hamycin, ichthammol, iodine, itraconazole, ketoconazole, miconazole, nikkomycin Z, potassium iodide, potassium permanganate, pradimicin A, propylparaben, resorcinol, sodium benzoate, sodium propionate, sulconazole, terconazole, tolnaftate, triacetin, unidecyleneic acid, monocyte-macrophage colony stimulating factor (M-CSF) and zinc unidecylenate. Of these, preferred are candicidin, clotrimazole, econazole, fluconazole, griseofulvin, hamycin, itraconazole, ketoconazole, miconazole, sulconazole, terconazole, and tolnaftate.

In one particular embodiment of the invention, the antifungal dry powder comprises an antifungal other than an azole-containing antifungal agent (e.g., the powder does not contain azoles such as clotrimazole, econazole, fluconazole, itraconazole, ketoconazole, or miconazole).

In yet another embodiment of the invention, the components (i.e., the antifungal compound and optional carriers/excipients) comprise a homogeneous spray-dried powder rather than an admixture of dry powder or particulate components. In yet another embodiment, the antifungal compound (e.g., polyene) is not protected by sequestration within liposomes or by a polymeric encapsulating agent, or by a discrete coating layer, but rather, is directly exposed to the harsh conditions of spray-drying during formation of the spray dried antifungal powder. That is to say, the compositions of the present invention typically are those in which the polyene is non-encapsulated. Additionally, the compositions of the invention are typically absent substantial amounts of polymer additives, such as those employed in sustained release-type formulations or non-biological polymers. For example, representative formulations will typically contain no more than about 10% by weight polymer, more preferably no more than about 5% by weight polymer, and even more preferably no more than about 3% polymer additive.

Compositions in accordance with the invention comprise a therapeutically effective amount of an antifungal compound, preferably a polyene such as amphotericin B. The amount of antifungal contained in the powder particles will be that amount necessary to pulmonarily deliver a therapeutically or prophylactically effective amount (i.e., a fungistatic and/or fungicidal amount) of the antifungal compound over the course of a particular dosing regimen at the site of infection. In practice, this will vary widely depending upon the particular antifungal compound and its corresponding potency, the particular fungal condition to be treated or prevented and its severity, the intended patient population, and similar considerations, and can be readily determined by one skilled in the art. A notable advantage of the respirable compositions described herein is their ability, in the case of pulmonary fungal infections, to be delivered directly to the site of infection—the lung. This allows for the administering of lower overall doses of antifungal than are typically administered orally or intravenously to achieve the same level of fungistatic or fungicidal action, which can also reduce the potential for adverse side effects in the patient. Moreover, due to the highly dispersible nature of the antifungal powders of the invention, losses to the inhalation device are minimized, meaning that more of the powder dose is actually delivered to the patient.

Dry powder formulations will generally comprise from about 0.1% to 100% by weight of a polyene, preferably from about 5% to about 100% by weight polyene, more preferably from about 20% to about 100% by weight polyene, and most preferably will comprise greater than about 30% by weight polyene. Particular powders of the invention are those comprising one of the following percentages by weight polyene antifungal compound: 1%, 3%, 5%, 10%, 15%, 20%, 25%, 30%, 35%, 40%, 45%, 50%, 55%, 60%, 65%, 70%, 75%, 80%, 85%, 90%, 95%, or 100%. Particularly preferred are dry powder compositions containing at least about 30% to 50% or more polyene. The antifungal powders are particularly useful for antifungals that are administered to the lung in doses of from 1 mg/day to 200 mg/day, preferably 5 mg/day to 100 mg/day.

B. Excipients

In the compositions of the invention, an antifungal compound, preferably a polyene, is optionally but not necessarily combined with one or more pharmaceutical excipients that are suitable for respiratory and pulmonary administration. Such excipients may serve simply as bulking agents when it is desired to reduce the active agent concentration in the powder that is being delivered to a patient. Preferred are excipients that can also serve in one or more of the following capacities: (i) improve the dispersibility and aerosol performance of a powder within a powder dispersion device in order to provide more efficient and reproducible delivery of the compound, (ii) improve the handling characteristics of the powder (e.g., flowability and consistency) to facilitate manufacturing and filling into unit dosage forms, and (iii) improve chemical and/or physical stability. In particular, the excipient materials can often function to optimize the residual moisture content, hinder excessive moisture uptake, influence particle size, the degree of aggregation, particle surface properties (i.e., rugosity), ease of inhalation, and targeting of the resultant particles to the lung tissue including the deep lung.

Alternatively, and in one preferred embodiment of the present invention, the antifungal, preferably a polyene, may be formulated in an essentially neat form, wherein the composition contains antifungal particles within the requisite size range and substantially free from other biologically active components, pharmaceutical excipients, and the like.

Alternatively, the antifungal may be formulated in an essentially neat form but complexed with a deoxycholate salt, by adding sodium deoxycholate or another deoxycholate salt to form an aqueous solution, wherein the composition contains antifungal particles within the requisite size range and substantially free from other biologically active components, pharmaceutical excipients, and the like. The sodium deoxycholate enhances solubilization of the antifungal agent, amphotericin B in particular, in water at a pH that is especially conducive to good chemical stability and yet, surprisingly, produces particularly dispersible powders (see, for example, Example 2).

Pharmaceutical excipients and additives useful in the present composition include but are not limited to proteins, peptides, amino acids (which are preferably non-acylated or non-sulfonated), lipids (which, if employed are typically not encapsulating agents, i.e., liposomes), and carbohydrates (e.g., sugars, including monosaccharides, disaccharides, trisaccharides, tetrasaccharides, and oligosaccharides; derivatized sugars such as alditols, aldonic acids, esterified sugars and the like; and polysaccharides), which may be present singly or in combination. Also preferred are excipients having glass transition temperatures (Tg), above about 35° C., preferably above about 45° C., more preferably above about 55° C. Illustrative excipients suitable for use in the compositions described herein include those described in Inhale Therapeutic Systems' International Patent Application No. WO 98/16207.

Exemplary protein excipients include serum albumin such as human serum albumin (HSA), recombinant human albumin (rHA), gelatin, casein, and the like. Polypeptides and proteins suitable for use in the dry powder composition of the invention are provided in Inhale Therapeutic Systems' International Patent Publication No. WO96/32096. HSA is a preferred proteinaceous excipient, and has been shown to increase the dispersibility of dry powders for aerosolized delivery to the lungs (WO 96/32096, ibid). However, as shown by the Examples contained herein, the powders of the invention display good dispersibilities, even in the absence of dispersibility-enhancing agents such as HSA and the like.

Representative amino acid/polypeptide components, which may optionally function in a buffering capacity, include alanine, glycine, arginine, betaine, histidine, glutamic acid, aspartic acid, cysteine, lysine, leucine, isoleucine, valine, methionine, phenylalanine, aspartame, threonine, tyrosine, tryptophan and the like. Preferred are amino acids and peptides that can also function as dispersibility-enhancing agents. Amino acids falling into this category include hydrophobic amino N acids such as leucine (leu), valine (val), isoleucine (isoleu), norleucine, tryptophan (try) alanine (ala), methionine (met), phenylalanine (phe), tyrosine (tyr), histidine (his), and proline (pro). One particularly preferred amino acid is the amino acid, leucine. Leucine, when used in the formulations described herein includes D-leucine, L-leucine, racemic leucine, and combinations of D- and L-leucine at any ratio. Dispersibility enhancing peptides for use in the invention include dimers, trimers, tetramers, and pentamers composed of hydrophobic amino acid components such as those described above, e.g., di-leucine and tri-leucine. Further examples include di-valine, di-isoleucine, di-tryptophan, di-alanine, and the like, tri-valine, tri-isoleucine, tri-tryptophan, etc.; mixed di- and tri-peptides, such as leu-val, isoleu-leu, try-ala, leu-try, etc., and leu-val-leu, val-isoleu-try, ala-leu-val, and the like, and homo-tetramers or pentamers such as tetra-alanine and penta-alanine. Preferred are amino acids and oligomers containing from 1-5 amino acid residues, and more preferably containing 1-3 amino acid residues and containing at least one (i.e., one or more) leucyl-residue. Illustrative dimers and trimers for use in the antifungal compositions of the invention are provided in International Patent Application No. PCT/US00/09785, entitled, "Dry Powder Compositions Having Improved Dispersivity", the disclosure of which is incorporated herein by reference in its entirety.

Preferred are compositions comprising at least 10% by weight of a leucyl-containing excipient, e.g., leucine, dileucine or trileucine, and more preferably at least 25% to 30% by weight of a leucyl-containing excipient as described above. Representative powder compositions in accordance with the invention comprise one of the following percentages by weight excipient, preferably a leucyl-containing excipient such as leucine, dileucine or trileucine: 5%, 10%, 15%, 20%, 25%, 30%, 35%, 40%, 45%, 50%, 55%, 60%, 65%, 70%, 75%, or 80% or more excipient. Representative formulations are provided in the Examples.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; trisaccharides such as melezitose and raffinose; polysaccharides, maltodextrins, dextrans, starches, and the like; and alditols, such as mannitol, xylitol, maltitol, lactitol, xylitol, sorbitol (glucitol), myoinositol and the like. Preferred carbohydrate excipients for use in the present invention include mannitol, trehalose, and raffinose.

The dry powder compositions may also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid; phthalic acid, Tris, and tromethamine hydrochloride. Commonly used inorganic acids/buffers include hydrochloric acid, sulfuric acid, boric acid, carbonic acid and phosphoric acid. Preferred buffers for use in the compositions of the invention are citrate and phosphate buffer.

Additionally, the formulations of the invention may include small amounts of polymeric excipients/additives such as polyvinylpyrrolidones, derivatized celluloses, such as hydroxymethylcellulose, hydroxyethylcellulose, or hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, polyamino acids (e.g., polyleucine, polyglutamic acid), pectin, generally where such polymers are present as powder additives rather than as encapsulating or coating agents or as components of a polymeric matrix.

The composition of the invention may also optionally contain flavoring agents, salts (e.g., sodium chloride), sweeteners, antioxidants, antistatic agents, surfactants (e.g., polysorbates such as "TWEEN 20" and "TWEEN 80"), lecithin, oleic acid, benzalkonium chloride, sorbitan esters, lipids (e.g., phospholipids, fatty acids), steroids (e.g., cholesterol), and chelating agents (e.g., EDTA). Other pharmaceutical excipients and/or additives suitable for use in the compositions of the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), and "Handbook of Pharmaceutical Excipients", (3rd Ed.), Vol. 3, Arthur H. Kibbe (Ed.), Ainley Wade, Paul J. Weller (1999), the disclosures of which are herein incorporated by reference.

The spray dried solid compositions in accordance with the invention may be crystalline, amorphous (i.e., glassy), or a mixture of both forms. Preferred are solid compositions that, irrespective of their percent crystallinity, are stable with respect to this percentage over time.

III. Preparing the Antifungal Formulations

Dry powder antifungal formulations of the invention are preferably prepared by spray drying. In general, spray drying is a process which combines a highly dispersed liquid and a sufficient volume of a hot gas to produce evaporation and drying of the liquid droplets to produce a powder. The preparation or feedstock can be a solution, suspension, slurry, or colloidal dispersion that is atomizable. Spray drying of an antifungal formulation is carried out, for example, as described generally in the Spray Drying Handbook, 5$^{th}$ ed., (1991), in European Patent Application EP 520 748 A1, in Inhale Therapeutics Systems' International Patent Publications, WO 97/41833 and WO 96/32149, or as described in International Patent Publication WO 99/16419, the contents of which are incorporated herein by reference.

In attempting to prepare a chemically stable, dispersible polyene dry powder for pulmonary administration, the inventors arrived at two processing approaches that (i) minimized the extent of degradation of polyene antibiotic, (ii) maintained a reasonable concentration of polyene in the pre-spray dried liquid composition (e.g., greater than about 1 mg/ml), and (iii) resulted in dispersible powders.

In one approach, which typically provides a uniform distribution of formulation components in the resulting, spray-dried particles (meaning that each of the particles in the final spray-dried formulation possesses substantially the same chemical composition and distribution of components within the particle), the feedstock comprises a polyene-containing solution. Preferred solvents are water, alcohols such as methanol or ethanol, and combinations thereof.

The challenge in utilizing this approach was to find a solvent or solvent system in which the polyene was both reasonably soluble (to an extent greater than 1 mg/mL) and relatively stable (i.e., exhibited less than about 10% degradation upon dissolution and spray drying). In the case of amphotericin B, which is essentially insoluble in water except at extremes of pH (e.g., pHs less than 3 and greater than 10), its solubility in water at neutral pHs can be significantly enhanced by complexation with a desoxycholate salt such as sodium desoxycholate or by adjustment of pH.

Utilizing the first approach, the polyene antifungal is first dissolved in water, optionally containing a physiologically acceptable buffer and/or complexing agent and/or acid or base to adjust the pH, as described above. The pH range of the resulting solution is preferably between about 4 and 10. The aqueous formulation may optionally contain additional water-miscible solvents, such as acetone, alcohols and the like as described above.

In yet another embodiment of the invention wherein the antifungal compound is spray dried as a solution rather than as a suspension, the antifungal compound (e.g., amphotericin B or nystatin) is dissolved in acidified alcohol. Representative alcohols are lower alcohols such as methanol, ethanol, propanol, isopropanol, and the like. One preferred alcohol is methanol. As shown in Example 4, extremes of pH, while improving the solubility of the representative polyene, amphotericin B, were deleterious to the chemical integrity of the drug, as shown in Table 6. Thus, the challenge was to optimize both solubility and chemical stability of the polyene. After extensive experimentation, an optimum range of pHs from about 3 to 6, preferably from about 3.5 to 6, even more preferably from about 3 to 5, and even more preferably from about 4 to 5, was determined for spray drying the polyene solutions of the invention (Examples 4-6). One particularly preferred pH range is from about 4.4 to 4.8, with pHs from about 4.8 to 6, and more preferably from about 4.8 to 5 being most preferred.

In further exploring ways to further improve the chemical stability of the polyene solutions, it was discovered unexpectedly that, for the polyene solutions examined, temperature had very little effect on solubility while having a profound effect on the rate of degradation of polyene. Thus, it was determined that low temperatures, e.g., below ambient or 25° C., preferably below about 8° C., and even more preferably at 0° C. or below, significantly improved the chemical stability of the solutions while not adversely impacting or significantly decreasing the solubility of the polyene in the solvent employed. In this respect, maintenance of the polyene solution at low temperatures such as those described above prior to spray drying (i.e., during and/or after dissolution) and/or as the feed solution, is effective to improve the chemical stability of the polyene to thereby form spray dried powders. Utilization of such conditions is typically effective to reduce the extent of degradation of the polyene to less than about 10%, and even more preferably less than about 5%.

Thus, particularly preferred conditions for spray drying a polyene solution that are effective to produce solubilities of polyene greater than about 1 mg/ml, more preferably greater than about 2 mg/ml, and even more preferably greater than about 3 mg/mil and maintain an extent of degradation of polyene of less than about 10%, are the utilization of acidified solvents such as methanol or ethanol or aqueous combinations thereof at pHs ranging from about 3.5 to 5, while optionally utilizing low temperature conditions as described herein for forming, and/or maintaining, and/or spray drying such solutions (Example 7). Additionally, powders thus formed were shown to possess good dispersibilities and aerodynamic diameters (Example 7).

In a second preferred approach for preparing the spray dried powders of the invention, a suspension of polyene is spray dried. In this approach, the polyene (e.g., amphotericin B), which, as supplied by the vendor, generally possesses a median particle size of from about 8 to 13 microns, is first suspended in an aqueous solvent such as water and subjected to wet milling. The wet milling process is effective to reduce the particle size of the polyene, typically to less than about 5 microns, and preferably to less than about 3 microns. Most typically, drug particles (and any optional undissolved excipient solids) are reduced to a size of about 1 micron or less during the process. Particle size reduction, and in particular, wet milling, is employed in the present process since, in the absence of such step, the spray dried particles will typically possess particle sizes that are too big for effective adminstration to the lung as a dry powder. Wet milling processes that may be employed include homogenization (e.g., using a pressurized spray type or ultrasonic homogenizer) or microfluidization.

Suspensions will generally contain about 1 mg/mL to about 100 mg/mL polyene, preferably from about 5 to about 100 mg/mL polyene, and even more preferably from about 5 to 20 mg/mL polyene. The wet milling step is effective to decrease both the particle size and distribution; the number of passes will typically range from about 1 to 10, although a plateau or leveling off of particle size reduction is typically achieved after about 3-5 passes. Surprisingly, no detectable degradation of polyene was observed during wet milling of the exemplary amphotericin suspensions of the invention. One exemplary method of wet milling for use in the method is homogenization (Example 8).

Optionally, one or more excipients as described above can be included in the suspensions of the invention. Such excipients may be added in either solution or dry form to the suspension prior to wet milling. Alternatively, one or more excipients in either dry or solution form may be added to the suspension after wet milling, or added in solution form as a co-spray dry solution during the spray drying step. Optionally, a buffer such as phosphate or citrate or the like is added to the wet milled suspension to form a suspension having near neutral pHs from about 6 to 8, or more preferably from about 7 to 8.

Alternatively, the polyene may be dry milled prior to suspension formation.

The aerosol properties of the spray dried powders, particularly but not necessarily those spray dried from suspensions, may be further improved by exposure of the spray dried powders to moisture. Specifically, it has been found that by exposing the spray dried powders, either during (e.g., using "wet" drying air) or post spray drying, to environments of controlled relative humidity, the aerodynamic diameters of such powders can be reduced, preferably to less than about 5 microns MMAD (Example 8). Preferably, the powders are exposed to a degree of moisture sufficient to increase to moisture content of the powders to greater or equal to about 3% or 3.5% by weight, with preferred moisture content of the powders ranging from about 4% to about 10% by weight. Preferred controlled relative humidity (RH) conditions are RHs greater than about 5%, with values typically ranging from about 5% to about 60%. While most spray dried powders are advantageously handled and packaged into unit dosage forms under dry conditions to optimize aerosol performance, aerosol performance (and mass median aerodynamic diameter in particular) of the powders of the invention was improved (i.e., decrease in MMAD) by increasing rather than decreasing their moisture contents. While not being bound by any theory, it appears that exposure of the powders to moisture is effective to bind water to the high energy sites on the surface of the polyene particles, to thereby decrease the tendency of the particles to aggregate.

Alternatively, higher level moisture environments can be achieved indirectly from the spray drying process itself by employing one or more of the following approaches: lowering the inlet temperature, e.g., to below about 80° C., e.g., to temperatures ranging from about 50° to 80° C., or from about 60° to 80° C.; increasing the suspension feed rate to greater than about 5 mL/min, for example to rates greater than about 10 mL/min, or, as described above, by use of a drying gas other than dry air, i.e., air or another inert gas at higher controlled relative humidities than dry air. Note that the exact operating conditions will vary, depending upon the particular processing unit employed.

Optionally, in-line sonication may also be employed to further reduce the particle size of the spray-dried polyene compositions of the invention. For instance, the feed suspension may be passed through a sonicator prior to atomization.

Additional spray drying processes which may be suitable for preparing the spray-dried antifungal compositions of the invention are described in U.S. Pat. Nos. 5,985,248; 5,976,574; 6,001,336, and 6,077,543, all assigned to Inhale Therapeutics Systems, Inc., the contents of which are expressly incorporated herein by reference.

Polyene-containing solutions/suspensions such as those described above are spray dried in a conventional spray drier, such as those available from commercial suppliers such as Niro A/S (Denmark), Buchi (Switzerland) and the like, resulting in dispersible, chemically stable antifungal dry powders. Optimal conditions for spray drying the polyene antifungal solutions/suspensions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause significant decomposition of the polyene antifungal in the sprayed material. Such temperatures are typically determined experimentally, although generally, the inlet temperature will range from about 50° C. to about 200° C., more preferably from about 60° C. to about 150° C., while the outlet temperature will range from about 30° C. to about 150° C.

An antifungal dry powder in accordance with the invention may also be prepared, although less preferably, by lyophilization, vacuum drying, spray freeze drying, super critical fluid processing, or other forms of evaporative drying. Such drying procedures will preferably be accompanied by additional processing steps, e.g., by blending, grinding or jet milling, to obtain an antifungal dry powder having suitable chemical, physical and aerosol properties suitable for administration into the deep lung.

In some instances, it will be desirable to prepare dry powder formulations possessing improved handling/processing characteristics, e.g., reduced static, better flowability, low caking, and the like, by preparing compositions composed of fine particle aggregates, that is, aggregates or agglomerates of the above-described dry powder particles, where the aggregates are readily broken back down to the fine powder components for pulmonary delivery, as described, e.g., Johnson, et al., U.S. Pat. No. 5,654,007, Aug. 5, 1997, incorporated herein by reference. Alternatively, the powders may be prepared by agglomerating the powder components, sieving the materials to obtain the agglomerates, spheronizing to provide a more spherical agglomerate, and sizing to obtain a uniformly-sized product, as described, e.g., and in Ahlneck, C.; et al., International PCT Publication No. WO95/09616, Apr. 13, 1995, incorporated herein by reference. The dry powders of the invention may also be prepared by blending, grinding or jet milling formulation components directly in dry powder form.

IV. Characteristics of Antifungal Powder Formulations

The antifungal compositions of the invention are further characterized by several features, most notably, the ability of the aerosolized composition to reach the tissues of the lung and lower respiratory tract. Passage of the particles into the lung physiology is an important aspect of the present invention, since the concentration of antifungal at the site of infection is an important feature in the successful treatment of pulmonary fungal infections. Indeed, certain physical characteristics of antifungal dry powders, to be described more fully below, are important in maximizing the efficiency of aerosolized delivery of such powders to the deep lung.

Polyene antifungal dry powders are composed of particles effective to penetrate into the alveoli of the lungs, that is, having a mass median diameter (MMD) from about 0.1 to 20 µm. Typically, the MMD of the particles is less than about 10 µm (e.g., ranging from about 0.1 to 10 µm), preferably less than 7.5 µm (e.g., ranging from about 0.5 to 7 microns), and most preferably less than 5 µm, and usually being in the range of 0.1 µm to 5 µm in diameter, depending upon the specific characteristics of the powder. In looking at representative powders in accordance with the invention (see, for example, Examples 1 and 3), the powders of the invention are most preferably although not necessarily characterized by extremely small particle sizes, of less than about 2 microns MMD. Such particles are extremely effective in targeting the lung when administered by inhalation.

In some cases, an antifungal powder composition will also contain non-respirable carrier particles such as lactose, where the non-respirable particles are typically greater than about 40 microns in size.

Antifungal powders of the invention are further characterized by an aerosol particle size distribution less than about 10 µm mass median aerodynamic diameter (MMAD), and preferably less than 5 µm, and more preferably less than about 3.5 µm. The above-described approaches for exposing the powders to high moisture environments are particularly effective in producing powders having MMAD values less than about 3.5 microns. The mass median aerodynamic diameters of the powders will characteristically range from about 0.5 to 5.0 µm, preferably from about 1.0 to 4.0 µm MMAD, more preferably from about 1.0 to 3.5 µm MMAD, and even more preferably from about 1.0 to 3.0 µm. As demonstrated in the Examples, illustrative antifungal powders having extremely small aerodynamic sizes, typically less than 3.5 microns, and often less than 2.0 microns, have been reproducibly prepared. This feature of the present powders is particularly advantageous, since large particles having diameters above 5 microns are typically removed by impaction in the upper airways (nose, mouth, pharynx, trachea and large bronchi), while those having aerodynamic sizes below 0.5 microns are generally exhaled. Thus, the present particles are beneficial for inhalation therapy due, in one aspect, to their ability to efficiently target the lung without extensive deposition in the upper airways.

Dry powder compositions of the invention will generally have a moisture content below about 15% by weight, usually below about 10% by weight, and preferably ranging from about 3.0% to about 10% by weight.

The powders of the invention are further characterized as relatively free-flowing rather than compacted solids.

The emitted dose or ED (sometimes also referred to as delivered dose efficiency, DDE) of these powders is greater than 30% and usually greater than 40%. More typically, the emitted dose of the antifungal powders of the invention is greater than 50%, and is often greater than 60%. Even more preferably, the ED of an antifungal powder is greater than 65%. Highly preferred are powders having ED values greater than 50% to 60% and MMADs of less than about 3.5 microns.

Powders of the invention will typically possess a bulk density value ranging from about 0.05 to 10 gram/cubic centimeter, preferably from about 0.05 to 5 gram/cubic centimeter, more preferably from about 0.10 to 4.0 grams/cubic centimeter, even more preferably from about 0.10 to 1 gram/cubic centimeter, even more preferably from about 0.10-0.75 gram/cubic centimeter, and most preferably from about 0.17 to 0.75 gram/cubic centimeter.

An additional measure for characterizing the overall aerosol performance of a dry powder is the fine particle fraction (FPF), which describes the percentage of powder having an aerodynamic diameter less than 3.3 microns. Antifungal powder compositions are particularly well suited for pulmonary delivery, and will possess FPF values ranging from about 45%-90%. Such powders contain at least about 45 percent of aerosol particle sizes below 3.3 µm to about 0.5 µm and are thus are extremely effective when delivered in aerosolized form, in (i) reaching the tissues of the lung, and, in the case of treatment of systemic fungal infections, (ii) reaching the alveolar region of the lung, followed by (iii) diffusion to the interstitium and (iv) subsequent passage into the bloodstream through the endothelium.

The particles of the invention also possess substantially intact polyene, that is to say, the amount of polyene degradation products is typically less than about 10% relative to the pre-spray dried control, and more preferably is less than about 5%. In other words, relative to the pre-spray dried starting material, the polyene remains at least 90% chemically intact or pure upon spray drying. Preferably, the spray dried powder contains at least 95% pure or chemically intact polyene relative to the pre-spray dried material.

The compositions described herein also possess good stability with respect to aerosol performance over time.

V. Pulmonary Administration of the Powder

Dry powder formulations as described herein may be delivered using any suitable dry powder inhaler (DPI), i.e., an inhaler device that utilizes the patient's inhaled breath as a vehicle to transport the dry powder drug to the lungs. Preferred are Inhale Therapeutic Systems' dry powder inhalation devices as described in Patton, J. S., et al., U.S. Pat. No. 5,458,135, Oct. 17, 1995; Smith, A. E., et al., U.S. Pat. No. 5,740,794, Apr. 21, 1998; and in Smith, A. E., et. al., U.S. Pat. No. 5,785,049, Jul. 28, 1998, herein incorporated by reference. When administered using a device of this type, the powdered medicament is contained in a receptacle having a puncturable lid or other access surface, preferably a blister package or cartridge, where the receptacle may contain a single dosage unit or multiple dosage units. Convenient methods for filling large numbers of cavities (i.e., unit dose packages) with metered doses of dry powder medicament are described, e.g., in Parks, D. J., et al., International Patent Publication WO 97/41031, Nov. 6, 1997, incorporated herein by reference.

Also suitable for delivering the antifungal powders described herein are dry powder inhalers of the type described, for example, in Cocozza, S., et al., U.S. Pat. No. 3,906,950, Sept. 23, 1974, and in Cocozza, S., et al., U.S. Pat. No. 4,013,075, Mar. 22, 1977, incorporated herein by reference, wherein a pre-measured dose of FSP dry powder for delivery to a subject is contained within a hard gelatin capsule.

Other dry powder dispersion devices for pulmonary administration of dry powders include those described, for example, in Newell, R. E., et al, European Patent No. EP 129985, Sept. 7, 1988); in Hodson, P. D., et al., European Patent No. EP472598, Jul. 3, 1996; in Cocozza, S., et al., European Patent No. EP 467172, Apr. 6, 1994, and in Lloyd, L. J. et al., U.S. Pat. No. 5,522,385, Jun. 4, 1996, incorporated herein by reference. Also suitable for delivering the antifungal dry powders of the invention are inhalation devices such as the Astra-Draco "TURBUHALER". This type of device is described in detail in Virtanen, R., U.S. Pat. No. 4,668,218, May 26, 1987; in Wetterlin, K., et al., U.S. Pat. No. 4,667,668, May 26, 1987; and in Wetterlin, K., et al., U.S. Pat. No. 4,805,811, Feb. 21, 1989, all of which are incorporated herein by reference. Other suitable devices include dry powder inhalers such as Rotahaler® (Glaxo), Discus® (Glaxo), Spiros™ inhaler (Dura Pharmaceuticals), and the Spinhaler® (Fisons). Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in Mulhauser, P., et al, U.S. Pat. No. 5,388,572, Sept. 30, 1997, incorporated herein by reference.

An inhaleable antifungal composition may also be delivered using a pressurized, metered dose inhaler (MDI), e.g., the Ventolin® metered dose inhaler, containing a solution or suspension of drug in a pharmaceutically inert liquid propellant, e.g., a HFC, chlorofluorocarbon or fluorocarbon, as described in Laube, et al., U.S. Pat. No. 5,320,094, Jun. 14, 1994, and in Rubsamen, R. M., et al, U.S. Pat. No. 5,672,581 (1994), both incorporated herein by reference.

Prior to use, a packaged antifungal dry powder is generally stored under ambient conditions, and preferably is stored at a temperature at or below about 25° C., and relative humidity (RH) ranging from about 30 to 60% or greater as described above.

VI. Therapeutic Applications

The antifungal powders of the invention, when administered pulmonarily, are particularly effective in the treatment of respiratory fungal infections. The powders, when inhaled, penetrate into the airways of the lungs and achieve effective concentrations in the infected secretions and lung tissue, including the epithelial lining fluid, alveolar macrophages, and neutrophils, typically exceeding the $MIC_{90}$s of most respiratory fungal pathogens. Moreover, the doses of antifungal compound that are administered pulmonarily are typically much less than those administered by other routes and required to obtain similar antifungal effects, due to the efficient targeting of the inhaled powder directly to the site of fungal infection.

The powders of the present invention are useful in the prophylaxis of pulmonary fungal infections, particularly for immunocompromised patients, such as individuals undergoing chemotherapy or radiation therapy for cancer, organ transplant recipients, patients suffering from conditions that adversely affect the immune system such as HIV, or any other condition which predisposes a subject to pulmonary fungal infections. The powders are also advantageous for use in the treatment of active pulmonary fungal infections, such as aspergillosis (most commonly due to *Aspergillus fumigatus, Aspergillus flavus, Aspergillus niger, Aspergillus nidulans,* and *Aspergillus terreus*), coccidioidomycosis, histoplasmosis, blastomycosis, and other fungal pathogens.

For prophylaxis, the amount per dose of antifungal agent is that amount that is effective to prevent pulmonary infection by a fungus is generally between about 0.01 mg/kg to about 5.0 mg/kg. Preferably, the amount per dose of the antifungal (e.g., polyene) that is administered by inhalation to a subject in need thereof is typically from about 0.4 mg/kg to about 4.0 mg/kg, or even more preferably from about 0.7 mg/kg to about 3.0 mg/kg. A powder in accordance with the invention is administered to a subject in any regimen which is effective to prevent pulmonary infection by a fungus. Illustrative prophylactic regimes include administering an antifungal dry powder as described herein 1 to 21 times per week over a time course from 1 to 26 weeks, followed, if needed, thereafter by administration once or twice weekly. A suitable subject for receiving treatment as described herein is any mammalian subject in need thereof, preferably such mammal is a human.

For treating a subject suffering from a pulmonary fungal infection, the amount per dose of antifungal agent administered by oral inhalation is that amount which is effective to treat the infection. The amount of antifungal agent for the treatment of infection will generally be higher than that used for prevention, and will typically range from about 0.01 mg/kg to 7.0 mg/kg. Preferably, the amount administered will be from about 0.2 mg/kg to about 6.0 mg/kg, and more preferably from about 0.8 mg/kg to about 5.0 mg/kg. In one exemplary treatment regimen, an antifungal powder in accordance with the invention is administered 1 to 8 times daily, preferably from 2-6 times daily, over a course of from about 7 to about 183 days.

In treating these respiratory fungal conditions, the powders of the invention are typically administered in doses that are 3-10 or more times the $MIC_{90}$ of the causative fungal pathogens; these levels are safely achievable by inhalation. Generally, the dose of antifungal compound delivered to a subject will be from about 2 mg to about 400 mg daily, preferably from about 10 to 200 milligrams daily, depending upon the particular antifungal compound, the condition being treated, the age and weight of the subject, and the like. The antifungal powder, when administered via a dry powder inhaler, is typically administered in unit dose form, with unit dose sizes varying from about 2 milligrams to 250 milligrams, and more preferably from about 5 milligrams to 100 milligrams. From one up to about 10 unit doses are generally administered daily during the course of therapy, although more preferably a treatment regimen will consist of from one to about 8 unit doses daily by inhalation.

The compositions of the invention offer several notable advantages: (i) increased antifungal protection at drug entry site, (ii) elimination or minimization of undesirable side effects without a concomitant increase in renal toxicity, (iii) result in mimimal or undetectable levels of antifungal compound in non-target tissues, (iv) reduce the fungal burden in the respiratory tract to thereby decrease chronic antigenic stimulation, reduce inflammatory response, and ameliorate symptoms, (v) possibly reduce the long term risk of progression or slow progression, and (vi) are conveniently administered.

The disclosure of each publication, patent or patent application mentioned in this specification is incorporated by reference herein to the same extent as if each individual publication, patent or patent application were specifically and individually indicated to be incorporated by reference.

The following examples illustrate, but in no way are intended to limit the scope of the present invention.

Experimental

Materials and Methods

The following materials were employed. The grades and manufacturers are representative of many that are suitable.

Materials

Amphotericin B (Spectrum, New Brunswick, N.J.; Alapharma)

Nystatin (Spectrum, New Brunswick, N.J.)

Methanol dehydrated, HPLC grade (EM Industries, Gibbstown, N.J.)

Sodium Hydroxide, 50% (J. T. Baker, Phillipsburg, N.J.)

L-Leucine (Aldrich)

Hydrochloric Acid (J. T. Baker, Phillipsburg, N.J.)

Sodium Deoxycholate (Spectrum, New Brunswick, N.J.)

Methods

Reverse Phase-HPLC

RP-HPLC analysis was performed on a Waters 2690HPLC system with a Waters Detector 996 (Skywalker, Inhale No.101232). The system was equipped with either a Vydac C-18 column or an YMC ODC-AQ™ C-18 column. Samples were eluted with a gradient mobile phases consisted of 10 mM sodium acetate buffer (mobile phase A) at pH 5 and CAN (mobile phase B). The flow rate was maintained at 1.0 ml/min, the detector wavelength was 383 nm, and the injection volume was 30μL (microliter).

Stability Samples

Blisters from the stability formulations were placed into 25° C. and 40° C. temperature stations (Temperature stations: 40° C./75RH: Environmental Specialties, Inc.; 25° C./60RH: Environmental Specialties, Inc).

The blisters were sealed in an aluminum bag with desiccants. Samples were removed from the temperature station at predetermined time points.

EXAMPLE 1

Inhaleable Amphotericin B Dry Powder Formulations

A. Finding A Suitable Solvent For Spray Drying

The solubility of amphotericin and excipients/additives of interest was determined in various solvents in an attempt to find a solvent system suitable for spray drying (i.e., having a sufficiently high vapor pressure) and capable of dissolving both amphotericin and any added excipients at an extent greater than about 10 mg/mL solvent. Although active agents can be spray-dried as suspensions, having the formulation components dissolved in solution provides resulting particles having a homogeneous composition (i.e., when comparing one particle to another particle)—that is to say, each particle in the composition has approximately the same composition and distribution of formulation components.

Amphotericin B is difficult to spray dry due to its poor solubility in water at any pH where it is likely to have reasonable stability (amphotericin is insoluble in water at pH 6 to 7). Amphotericin B is soluble in water at pHs lower than 3 and higher than 10, but only to a limited extent (0.2 mg/ml) —making the volume of solvent required for spray drying under these conditions too large to be reasonably handled. Thus, the following solubilities were experimentally determined to find a single (non-mixed) solvent system for spray drying representative amphotericin B and nystatin formulations.

TABLE 1

Solubility of Representative Polyenes and Excipients

| | Solubility (mg compound/g solvent) | | |
|---|---|---|---|
| Solvent | Amphotericin | Nystatin | Leucine |
| DI Water | 0.2 | 1.1 | Not performed |
| IPA | 0.1 | 0.1 | 0.8 |
| Methanol | 1.5 | 11.0 | 2.6 |
| Ethanol | 0.2 | 0.8 | 1.2 |
| Hexane | 0.0 | 0.0 | 7.0 |
| Acetone | 0.2 | 0.1 | 1.7 |
| Pet. Ether | 0.0 | 0.0 | 0.8 |
| Ethyl Ether | 0.2 | 0.1 | 0.8 |

TABLE 1-continued

Solubility of Representative Polyenes and Excipients

| | Solubility (mg compound/g solvent) | | |
|---|---|---|---|
| Solvent | Amphotericin | Nystatin | Leucine |
| Chloroform | 0.2 | 0.7 | 1.2 |
| Isobutyl Alcohol | 0.0 | 0.5 | Not performed |
| Meth. Chloride | 1.5 | 3.9 | 1.8 |
| IP Acetate | 0.0 | 0.1 | 0.7 |
| THF | 0.6 | 1.6 | 0.8 |

Neither water nor any pure pharmaceutically acceptable solvent appeared to be able to jointly dissolve amphotericin B and one particularly preferred excipient, leucine, at the desired levels. However, when acidified with an acid such as hydrochloric acid, methanol was effective in dissolving both amphotericin B and leucine at acceptable levels, that is, at combined solids concentrations of at least about 10 mg/ml.

B. Preparing Dry Powders

The antifungal and solid excipient (where employed) were mixed with methanol at a 1% w/w solids concentration to form a suspension. The pH of the medium was adjusted (acidified) with hydrochloric acid while stirring continuously and/or sonicating to facilitate solubilization of the components. The pH was adjusted until all of the components were in solution. The goal was to utilize the least acidic condition possible that resulted in complete solubilization, to minimize the chemical destabilization of the components in the solution. Sodium hydroxide was added to further adjust the pH if needed. The resulting solution was then spray dried.

All batches were spray dried using a modified Buchi 190 Mini Spray Dryer supplied with nitrogen as the gas source and equipped with an oxygen level sensor. The solution feed rate was 5 ml/minute, the inlet temperature was adjusted to obtain an outlet temperature of approximately 80° C., the drying gas flow rate was about 18 SCFM, and the atomizing air was supplied at 0.5 to 1.5 SCFM, typically at a pressure of about 100 PSI.

The characteristics of each of the formulations prepared and the characteristics of the resulting powders are provided in Table 2 below.

TABLE 2A

Aerosol Characteristics of Illustrative Spray Dried Polyene Powders

| Drug Formulation, by weight percent | Lot No. | pH of Solution | % Resid. Solvent* | % ED ± RSD | MMAD | Particle Morphology |
|---|---|---|---|---|---|---|
| Amphotericin | 1696-HS-35 | 5.1** | 1.6 | 63 ± 6 | 1.9 | Raisin-like |
| 90% Amphotericin + 10% L-Leucine | 1696-HS-36 | 3.1 | 3.0 | 63 ± 5 | 2.4 | Mostly collapsed hemispheres |
| 75% Amphotericin + 25% L-Leucine | 1696-HS-37 | 2.9 | 2.9 | 81 ± 6 | 1.9 | Raisin-like |

*Residual solvent content was determined by thermogravimetric analysis.
**The accuracy of this result is in question; the true value may be lower.

TABLE 2B

Aerosol Characteristics of Illustrative Spray Dried Polyene Powders

| Drug Formulation, by weight percent | % <3.3 μm | MMD μm |
|---|---|---|
| Amphotericin | 70 | 0.6 |
| 90% Amphotericin + 10% L-Leucine | 65 | 0.8 |
| 75% Amphotericin + 25% L-Leucine | 80 | 0.6 |

Spray drying neat amphotericin B dissolved in acidified methanol provided a powder having a good dispersibility (an emitted dose of 63%) and a superior MMAD of 1.9 microns. The aerosol properties of the neat formulation were surprising, particularly in view of the (i) absence of stabilizing or dispersibility enhancing excipients, and (ii) the non-protein nature of the active agent. While proteins and polypeptides have been demonstrated to have dispersibility-enhancing characteristics when employed in dry powder formulations (U.S. Pat. No. 6,136,346), it is unusual to spray-dry a non-proteinaceous active agent to form a highly dispersible powder. The addition of 10% by weight leucine did not materially change the characteristics of the powder, however, when the amount of leucine contained in the powder was increased to 25% by weight of the composition, a significant improvement in emitted dose was achieved (from 63% to 81%), without compromising the MMAD value. This was also surprising, since typically these two factors, emitted dose and aerodynamic diameter, work in opposing fashions. That is to say, generally, an increase or improvement in ED is often accompanied by an undesirable increase in aerodynamic diameter, since larger particles tend to agglomerate less and thus disperse better. That is to say, it is generally thought that larger particles tend to exhibit fewer cohesive forces due to the inverse relationship between Van der Waals forces and particle size, and also due to a decreased impact of electrostatic forces on larger particles. Thus, it is unusual to prepare non-protein containing dry powders which possess both excellent EDs (greater than 50%, preferably greater than 60%, more preferably greater than 80%) and superior aerodynamic diameters (less than about 5 microns, preferably less than about 3.5 microns, more preferably less than about 3 microns, and even more preferably less than about 2 microns).

EXAMPLE 2

Inhaleable Amphotericin B Dry Powder Formulations Containing Deoxycholate

A. Preparing Dry Powders

Sodium deoxycholate was dissolved in water. Amphotericin was added to the sodium deoxycholate solution, and sonicated. 6 molar sodium hydroxide was slowly added to the mixture while stirring and/or sonicating, until the amphotericin was dissolved. The pH of the resulting solution was adjusted (acidified) to 7.0-7.5, while stirring, with 1.2 normal hydrochloric acid. The solution was protected from light. The aim was to utilize the most neutral solution possible that resulted in complete solubilization, to minimize or essentially eliminate any chemical destabilization of the components in the solution. The resulting solution was then spray dried as detailed in Example 1.

The characteristics of each of the formulations prepared and the characteristics of the resulting powders are provided in Table 3 below.

TABLE 3A

Amphotericin B/Sodium Deoxycholate Powder Preparation: Formulation Parameters

| | Quantity per Batch | |
|---|---|---|
| Ingredient | Batch 2242-AA-57 | Batch 2242-AA-60 |
| Amphotericin B | 0.700 g | 0.825 g |
| Sodium Deoxycholate | 0.314 g | 0.1848 g |
| DI Water | 100 ml | 165 ml |
| 12 N and/or 1.2 N HCl | 0.925 ml | 0.225 ml |
| 6 M NaOH | 0.162 ml | 0.225 ml |

TABLE 3B

Amphotericin B With Sodium Deoxycholate: Powder Characteristics

| Batch # | 2242-AA-57 | 2242-AA-60 |
|---|---|---|
| Molar Ratio Amphotericin B/Sodium Deoxycholate | 1.0 | 2.0 |
| Final Solution pH | 7.5 | 7.3 |
| Amphotericin B/Sodium Deoxycholate Solution Concentration (mg/ml) | ~7.0/3.1 | ~5.0/1.1 |
| % ED ± % RSD | 72 ± 4 | 75 ± 3 |
| MMAD (μm) | 2.8 | 2.6 |
| % <3.3 μm | 62 | 67 |
| % Moisture Content (by TGA) | 2.5 | Not available |

Spray drying a nearly neutral pH aqueous solution of amphotericin B with sodium deoxycholate provided a powder having a good dispersibility (an emitted dose of greater than 70%) and a good MMAD of less than 3.0 microns

EXAMPLE 3

Inhaleable Dry Powder Formulations of Nystatin

The solubility of nystatin and leucine in various solvents was explored to identify a solvent for preparing a spray-dried powder of the invention; solubility results are provided in Example 1 above.

Dry powders were prepared as described in Example 1 above using acidified methanol as the solvent. The characteristics of the resulting powders are summarized below.

TABLE 4A

Inhaleable Formulations of Nystatin: Composition Characteristics

| Drug Formulation | Lot No. | pH of Solution | % Residual Solvent | % ED ± RSD | MMAD | Morphology |
|---|---|---|---|---|---|---|
| Nystatin | 1696-HS-40 | 3.0 | 1.6 | 74 ± 4 | 1.6 | Dimpled spheres |
| 75% Nystatin + 25% L-Leucine | 1696-HS-42 | 3.9 | 1.8 | 79 ± 3 | 1.5 | Highly dimpled spheres |

TABLE 4B

Inhaleable Formulations of Nystatin: Composition Characteristics

| Drug Formulation | % <3.3 μm | MMD μm |
|---|---|---|
| Nystatin | 84 | 0.8 |
| 75% Nystatin (w/w) 25% L-Leucine (w/w) | 88 | 0.6 |

Spray drying neat nystatin dissolved in acidified methanol yielded a powder with a good emitted dose of greater than 70% and a superior MMAD of 1.6 microns. The addition of 25% leucine to the formulation resulted in a nominal improvement in emitted dose to 79% without compromising the MMAD (1.5 microns). Again, the superior aerosol properties of these powders, particularly the neat powders, were surprising in view of the lack of dispersibility enhancing agents such as proteins or polypeptides in the formulation. An optimized formulation comprising 25% leucine was identified.

EXAMPLE 4

Optimization of Low pH Solution Spray Drying Conditions for Amphotericin

Exemplary amphotericin B solutions were prepared and their solubilities and chemical stabilities were evaluated. The solutions were spray dried, and the chemical stabilities of the spray dried powders were also assessed.

TABLE 5

Composition of AmB formulations

| | | | % of Total Solid | | | | Total solid | |
|---|---|---|---|---|---|---|---|---|
| Formulation | Description | pH adjustment | AmB | SDC | Leu | Na/Cl | (%) | Final pH |
| R01013 | AmB in MeOH | Acidified to pH 1.4 | 96.5 | 0.0 | 0.0 | 3.5 | 1.0 | 4.0 |
| R01017 | AmB in MeOH/Leu | Acidified to pH 1.0 | 68.6 | 0 | 22.0 | 9.4 | 1.1 | 3.6 |

*SDC: Sodium Deoxycholate

The solutions were spray dried at a feed rate of approximately 5 mL/min and atomization pressures ranging from about 80-150 psi. The batch sizes was 1.5 liters for both formulations, with yields ranging from about 30-40%. Formulations R01011 and R01013 were placed in the temperature stations after filling into unit dosage forms (blisters). The chemical stability of AmB in both R01013 and R01017 was very poor at initial time point (Table 6).

TABLE 6

Chemical stability of AmB

| | | | | % AmB in sample | | |
|---|---|---|---|---|---|---|
| | | | | | T= 1 month | |
| Formulation | Description | Rec. pH | Pre-SD | T = 0 | 25° C. | 40° C. |
| R01013 | AmB in MeOH | 4.3 | | 45 | | |
| R01017 | AmB/Leu in MeOH | 3.7 | | 32 | | |

EXAMPLE 5

Optimization of Low pH Solution Spray Drying Conditions for Amphotericin

In an attempt to reduce the extent of chemical degradation of amphotericin, while also finding solution conditions under which amphotericin B was reasonably soluble (e.g., to an extent greater than about 1 mg/mL), solubility experiments were conducted. The experiments were performed at room temperature for the first 2 hour while adjusting for solution pH. After the amphotericin B was completely dissolved, the samples were transferred to a 4° C. refrigerator for further chemical stability analysis. Table 7 summarizes the formulation details and apparent solubilities at specific pH conditions. Table 8 shows the chemical stability of amphotericin B at 2 hours and 8 hours, as determined by RP-HPLC.

TABLE 7

Apparent Solubility of AmB in MeOH Formulations

| | | pH adj. | | | | % of Total Solid | | Total |
|---|---|---|---|---|---|---|---|---|
| | | Na | Cl | AmB | | AmB | Na/Cl | Solid |
| Formulation | pH | (mg/mL) | (mg/mL) | (mg/mL) | (mM) | (%) | (%) | (mg/mL) |
| 2452-36-3 | 4.4 | 0 | 0.07 | 2.92 | 3.16 | 97.6 | 2.4 | 3 |
| 2452-36-1 | 6.9 | 0 | 0 | 0.58 | 0.63 | 100 | 0 | 0.58 |
| 2452-36-2 | 9.6 | 0.01 | 0 | 0.95 | 1.02 | 98.8 | 1.2 | 0.96 |

TABLE 8

Chemical stability of Amphotericin in the formulations

| Formu- | | AmB %, T = 2 hr | | AmB %, T = 8 hr | |
|---|---|---|---|---|---|
| lation | pH | AmB (%) | Main Peak (%) | AmB (%) | Main peak (%) |
| 2452-36-3 | 4.4 | 93 | 91.1 | 92 | 91.2 |
| 2452-36-1 | 6.9 | 98 | 91.8 | 98 | 91.7 |
| 2452-36-2 | 9.6 | 96 | 92.4 | 96 | 93 |

As shown in formulation 2452-36-3, the apparent AmB solubility was 2.9 mg/mL, while the chemical stability was 92% at 8 hours. Based upon these favorable results (i.e., good solubility and stability), this formulation was further spray dried at various conditions as shown in Table 9. The solutions were spray dried utilizing atomization pressures ranging from about 25-60 psi. Chemical stability of the resulting powder was also evaluated.

TABLE 9

Spray drying condition and chemical stability

| Samples | pH | Feet rate (mL/min) | AmB % | MAIN PEAK % |
|---|---|---|---|---|
| Pre-spray dry solution, t = 0 | 4.4 | | 103 | 90.7 |
| Pre-spray dry solution, t = 7 hr | 4.4 | | 103 | 90.9 |
| R01037 powder | 4.4 | 5 | 78 | 70.8 |
| R01038 powder | 4.4 | 5 | 73 | 76.8 |
| R01039 powder | 4.4 | 7 | 70 | 72.1 |
| R01040 powder | 4.4 | 5 | 92 | 85.7 |

Thus, formulations were determined in which both solubility and chemical stability of the amphotericin were at acceptable levels. At pH 4.4 in methanol, amphotericin B exhibited an apparent solubility of 2.9 mg/mL, and the solution chemical stability was about 92% at 8 hours. Powders obtained by spray drying contained 92% intact amphotericin B when the outlet temperature was maintained below 80° C., at 50° C. The experiment also indicated that temperature is another key factor for improving the stability of amphotericin B upon formulation and spray drying.

EXAMPLE 6

Optimization of Low pH Solution Spray Drying Conditions for Amphotericin

Additional solubility of amphotericin B and stability of the representative formulation, R0140, was investigated. The solubility of amphotericin at pH 5 and at pH 4.7 was investigated; additionally, the chemical stability of amphotericin B at pH 4.8 was further examined. In these experiments, samples were placed in an ice bath during the formulation preparation. Results are listed in Table 10.

TABLE 10

Solubility and Stability of AmB in MeOH

| Samples | Temp. | Solubility (mg/mL) | AmB (%) | Main Peak % |
|---|---|---|---|---|
| AmB/MeOH, pH 4.7 | In ice | 3.4 | | |
| AmB/MeOH, pH 5.0 | In ice | 3.0 | | |
| AmB/MeOH, pH 4.8 | In ice | 3.0* | 97 | 92.0 |

*AmB concentration in the formulation

Even at low temperatures below ambient such as around 0° C. (ice bath) (solubility is known to decrease as temperature decreases), the solubility of AmB is approximately 3 mg/mL at pH 5 and 3.4 mg/mL at pH 4.7. That is to say, both of these are reasonable solubility levels of drug for spray drying. Additionally, the formulation at pH 4.8 demonstrated good chemical stability of AmB (97%) during the formulation preparation.

EXAMPLE 7

Chemical Stability of Amphotericin Versus Temperature

Solutions were prepared as follows. Amphotericin B (AmB) was added to MeOH (3 mg AmB/mL) at either room temperature or in an ice bath. Then 1N HCL was added to the solutions slowly with agitation to adjust the solution pH to 4.8 upon complete dissolution of amphotericin B. The chemical stability of AmB was determined by an HPLC assay as a function of time over 24 hours. The results are summarized in Table 11.

TABLE 11

Chemical stability of AmB as a function of time in MeOH at pH 4.8

| | % AmB | |
|---|---|---|
| Time (hr) | At Room Temperature | In Ice Bath |
| 1.5 | 89 | 97 |
| 4 | 85 | 99 |
| 6 | 83 | 97 |
| 8 | 84 | 94 |
| 24 | 78 | 97 |

Although the solubility of AmB increased at lower pHs (<pH 4.8), the chemical stability decreases. Using the same AmB solution preparation procedures as described above, the chemical stability of AmB at pH 3 and pH 4 in an ice bath is summarized below.

TABLE 12

Chemical stability of AmB in MeOH at different pHs in an ice bath

| Time (hr) | % AmB pH 3 | Time (hr) | % AmB pH 4 |
|---|---|---|---|
| 0.67 | 95 | 1 | 94 |
| 4 | 93 | 4 | 96 |
| 18.5 | 90 | 18.5 | 97 |
| 26 | 85 | 26 | 93 |

An AmB solution in MeOH at 3 mg/mL was spray dried; the aerosol properties of the resulting powders are provided below.

TABLE 13

Aerosol Properties

| Formulation | Lot # | ED (%) | MMAD (?m) |
|---|---|---|---|
| Neat AmB at pH 4.4 | R01041 | 49 | 2.6 |

EXAMPLE 8

Spray Drying Homogenized Suspensions of Amphotericin and Moisture Conditioning to Enhance Aerosol Performance The following describes the successful utilization of a suspension-based approach for preparing chemically stable, dispersible, inhaleable dry powders of amphotericin B.

A. Particle Size Reduction by Homogenization—General Preparation Method Employed Amphotericin B (median particle size 8-13 microns) was weighed and dispersed in water using a high shear mixer (Ultraturax) to achieve a uniform suspension. The suspension was passed through an Avestin C-5 homogenizer several times (1-5) at high pressures (~25,000 psi) under ambient conditions to reduce the particle size to less than about 1 micron, determined using a Malvern Mastersizer. Pressures ranging from about 5,000 to 30,000 psi can be utilized. The concentration of amphotericin in the suspension ranged from about 5-20 mg/mL, although suspensions with concentrations of polyene ranging from about 1 mg/mL to about 100 mg/mL can be utilized.

The homogenized suspensions were then spray dried using outlet temperatures ranging from about 60° C. to 80° C., a feed rate of 5 mL/min, and atomizer pressures ranging from 60-100 psi. The feed solids content ranged from 0.3-1.0% (w/v). HPLC analysis showed no degradation of Amphotericin B after homogenization and spray drying compared to the unprocessed drug (raw material) used as a control.

B. Formulations

Optional excipients were included in the formulations. Excipients were added to the formulations using various approaches: (i) an aqueous solution of excipient or solid excipient was added to/mixed with the homogenized aqueous suspension of amphotericin B followed by spray drying; or (ii) excipient was added to a suspension of amphotericin B prior to homogenization. Excipients included leucine, trileucine, raffinose, sodium citrate and sodium phosphate. During some of the spray drying runs, in-line sonication was employed to minimize aggregation of the particles.

C. Aerosol Properties of Homogenized, Spray Dried Powders.

TABLE 14

| Composition | MMAD (microns) | Emitted Dose, % |
| --- | --- | --- |
| 100% Amphotericin B (R01131-1) | 6.0 | 72 |
| 100% Amphotericin B (R01131-3) | 5.0 | 67 |
| Amphotericin B w/30% Raffinose (R01196) | 4.0 | Not done |
| Amphotericin B w/30% Leucine (R01198) | 3.9 | Not done |
| Amphotericin B w/sodium phosphate (pH 7.4), (R01199) | 4.7 | Not done |
| 100% Amphotericin B (R01101) | 5.55 | 61 |
| 100% Amphotericin B (R01115) | 4.72 | 71 |
| Amphotericin B with 30% Leucine (R01102) | 4.76 | 72 |
| Amphotericin B with 30% Trileucine (R01103) | 4.36 | 71 |

D. Chemical Stability

Degradation of amphotericin B was essentially undetectable both before and after homogenization. That is to say, amphotericin B was chemically stable under these process conditions.

TABLE 15

Chemical stability of AmB

| Formulation | Description | AmB (mg/mL) | % AmB in Formulation | % Main Peak |
| --- | --- | --- | --- | --- |
| Standard A | Mixing with Excipients to prepare for R01101 to R01103 | 11.6 | | 96.1 |
| Standard B | To prepare for R01104 | 12.8 | | 95.8 |
| R01101 | Neat AmB | | 96.2 | 96.3 |
| R01102 | AmB with 30% Leu | | 72.3 | 96.4 |
| R01103 | AmB with 30% Trileu | | 75.3 | 95.5 |
| R01104 | AmB with 5% DSPC/Ca$^{++}$ | | 89.3 | 96.1 |

E. Effect of Moisture

Neat Amphotericin B Formulations with different levels of moisture content were prepared by one of the two following methods:

(a) The spray dried powders were exposed to controlled environments of different relative humidity (Range 6% to 40% RH)

(b) Aqueous suspensions of Amphotericin B were spray dried under different conditions of outlet temperatures and feed rates to generate powders with different residual moisture contents.

Figure 1:
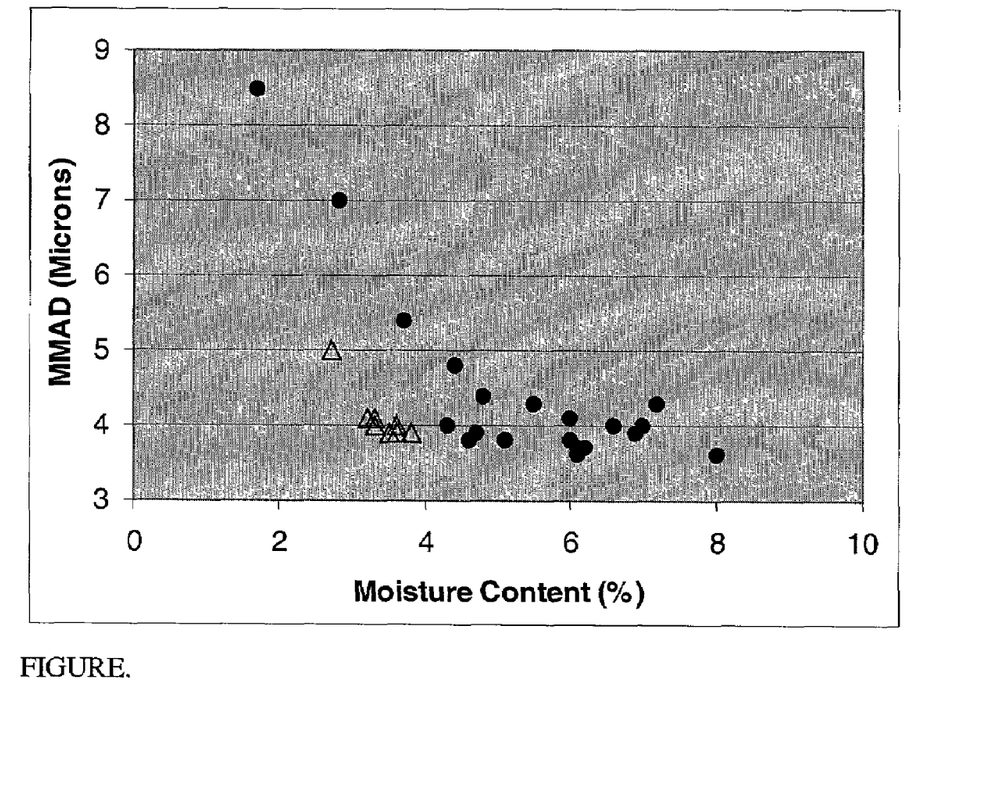
FIG. 1. The figure is a plot of MMAD as a function of moisture content of spray dried, neat Amphotericin B powders, the details of which are provided in Example 8. Solid circles represent powders in which moisture content was varied by exposure to controlled environments of different relative humidity (6-40%) and empty triangles represent powders in which moisture content was varied by changing the spray drying conditions.

The aerosol properties of the powders were tested. The following graph shows the correlation between MMAD and moisture content of neat Amphotericin B powders. For powders in which moisture was introduced by exposure to humidity after spray drying, the MMAD decreases with increase in moisture content up to about 4.0-4.5%. Beyond 4.5% moisture content, the MMAD is independent of moisture. A similar dependence of MMAD on moisture content is observed for powders in which moisture content was increased by spray drying under less aggressive conditions. However, the threshold moisture content beyond which the MMAD becomes independent of the moisture content appears to be about 3.5%. Thus, a minimum moisture content is necessary for improvement in the aerosol properties of spray dried powders containing Amphotericin B. However, the threshold moisture content beyond which the aerosol properties become independent of moisture content may differ depending upon the process used.

Amphotericin B powders containing excipients also show improvements in aerosol performance upon increase in moisture content. Excipient—containing Amphotericin B powders were filled into blisters under two different controlled relative humidity conditions and tested for MMAD. The data (in the table below) clearly shows that a significant reduction in MMAD can be achieved by increasing the moisture content of Amphotericin B powders (both in the absence and presence of excipients).

TABLE 16

Effect of moisture conditioning on MMAD of neat and excipient-containing Amphotericin B dry powder formulations

| Formulation | MMAD of powder filled at RH <5.0% (microns) | MMAD of powder filled at 40% RH (microns) |
|---|---|---|
| 100% Amphotericin B | 5.0 | 3.5 |
| 80% Amphotericin & 20% sodium phosphate | 3.6 | 2.9 |
| 70% Amphotericin B & 30% leucine | 3.3 | 2.5 |
| 70% Amphotericin B, 20% sodium phosphate & 10% leucine | 3.1 | 2.3 |

This finding is unexpected, since most spray dried powders either show better aerosol properties in the absence of moisture or are insensitive to moisture content. This phenomenon is likely due to water binding to the high energy sites located either on the surface of the Amphotericin B particles or within the crystal lattice. Such an association of water with Amphotericin B particles decreases their propensity to aggregate, thereby improving the aerosol performance of the powders.

It is claimed:

1. A dry powder for delivery by inhalation to the lungs, the dry powder produced by a method comprising:
   i) dissolving a polyene antifungal compound in an acidified solvent to form an acidic polyene-containing solution, and
   ii) spray drying said polyene-containing solution to form an inhaleable dry powder containing no more than about 10% polyene degradation products and characterized by an emitted dose greater than 60%.

2. A dry powder produced by a method comprising:
   i) suspending a polyene antifungal compound in an aqueous solvent to form a suspension,
   ii) wet milling the suspension from (i) to form a wet-milled suspension, and
   iii) spray drying the wet milled suspension to produce an inhaleable dry powder containing no more than about 10% polyene degradation products and characterized by an emitted dose greater than about 60%.

3. A spray-dried powder composition suitable for oral inhalation to the lung comprising a therapeutically effective amount of a polyene antifungal compound, wherein the composition comprises no more than about 10% polyene degradation products and is characterized by an emitted dose greater than about 60%.

4. The powder composition of claim 3, containing no more than about 5% polyene degradation products.

5. The powder composition of claim 3, wherein the powder comprises particles having an MMAD of less than about 5 microns.

6. The powder composition of claim 5, wherein the powder comprises particles having an MMAD of less than about 3.5 microns.

7. The powder composition of claim 3, which is non-proteinaceous.

8. The powder composition of claim 3, wherein said polyene is nystatin or amphotericin B.

9. The powder composition of claim 3, wherein said polyene is non-encapsulated.

10. The powder composition of claim 9, wherein said polyene is non-liposome and non-polymer encapsulated.

11. The powder composition of claim 3 substantially comprising neat polyene.

12. The powder composition of claim 3, further comprising a pharmaceutically acceptable excipient.

13. The powder composition of claim 12, wherein said excipient is selected from the group consisting of buffers, leucine, and trileucine.

14. The powder composition of claim 12, comprising at least about 30% by weight polyene.

15. The powder composition of claim 14, comprising at least about 50% by weight polyene.

16. The powder composition of claim 3, having a water content greater than about 4% by weight.

17. The powder composition of claim 16, having a water content ranging from about greater than 4% by weight to about 10% by weight.

18. A spray-dried powder composition suitable for oral inhalation to the lung comprising a therapeutically effective amount of a polyene antifungal compound and a leucyl-containing excipient comprising from 1 to 3 amino acid residues.

19. An aerosolized, spray-dried powder composition suitable for oral inhalation to the lung comprising a therapeutically effective amount of a polyene antifungal compound, wherein the composition comprises no more than about 10% polyene degradation products and is characterized by an emitted dose greater than about 60%.

20. A method for treating or preventing fungal infection in a subject in need thereof, said method comprising administering to said subject by oral inhalation a therapeutically effective amount of a spray dried powder composition of claim 3 in aerosolized form.

* * * * *